(12) United States Patent
Nam et al.

(10) Patent No.: US 10,695,282 B2
(45) Date of Patent: Jun. 30, 2020

(54) FUNCTIONALIZED TRANSITION METAL DICHALCOGENIDES AND COMPOSITION FOR ANTIOXIDATION CONTAINING THE SAME

(71) Applicants: AMOREPACIFIC CORPORATION, Seoul (KR); INDUSTRY-UNIVERSITY COOPERATION FOUNDATION HANYANG UNIVERSITY ERICA CAMPUS, Ansan-si, Gyeonggi-do (KR)

(72) Inventors: Jin Nam, Yongin-si (KR); Jong-Ho Kim, Ansan-si (KR); Jin Woong Kim, Seongnam-si (KR); Johnhwan Lee, Yongin-si (KR); Ji Eun Kim, Asan-si (KR); Dabin Yim, Changwon-si (KR)

(73) Assignees: AMOREPACIFIC CORPORATION, Seoul (KR); INDUSTRY-UNIVERSITY COOPERATION FOUNDATION HANYANG UNIVERSITY ERICA CAMPUS, Ansan-si, Gyeonggi-Do (KR)

( * ) Notice: Subject to any disclaimer, the term of this patent is extended or adjusted under 35 U.S.C. 154(b) by 43 days.

(21) Appl. No.: 15/957,398

(22) Filed: Apr. 19, 2018

(65) Prior Publication Data
US 2019/0216715 A1 Jul. 18, 2019

(30) Foreign Application Priority Data
Apr. 26, 2017 (KR) .......... 10-2017-0053805

(51) Int. Cl.
| | | |
|---|---|---|
| *A61K 8/90* | (2006.01) | |
| *A61K 8/23* | (2006.01) | |
| *A61Q 19/00* | (2006.01) | |
| *A61K 8/35* | (2006.01) | |
| *A61K 8/34* | (2006.01) | |
| *A61Q 5/12* | (2006.01) | |

(52) U.S. Cl.
CPC .............. *A61K 8/90* (2013.01); *A61K 8/23* (2013.01); *A61K 8/34* (2013.01); *A61K 8/35* (2013.01); *A61Q 19/00* (2013.01); *A23V 2250/1608* (2013.01); *A61K 2800/522* (2013.01); *A61Q 5/12* (2013.01)

(58) Field of Classification Search
None
See application file for complete search history.

(56) References Cited

FOREIGN PATENT DOCUMENTS

KR 101708260 B1 2/2017

OTHER PUBLICATIONS

Sim et al. "High-concentration dispersions of exfoliated MoS2 sheets stabilized by freeze-dried silk fibroin powder", Nano Research 2016, 9(6): 1709-1722 (Year: 2016).*
Kang et al. "Thickness sorting of two-dimensional transition metal dichalcogenides via copolymer-assisted density gradient ultracentrifugation", Nature Communications vol. 5, Article No. 5478 (2014) (Year: 2014).*
Ejaz et al. "Modular amphiphilic copolymer-grafted nanoparticles: "nanoparticle micelle" behavior enhances utility as dispersants", Polym. Chem., 2015, 6, 7749-7757 (Year: 2015).*

* cited by examiner

*Primary Examiner* — James W Rogers
(74) *Attorney, Agent, or Firm* — Cantor Colburn LLP

(57) ABSTRACT

Disclosed is a method for synthesizing antioxidant materials based on transition metal dichalcogenide (TMD) compounds and a technology of preparing a composition using the same. The monolayer TMDs functionalized with an amphiphilic block polymer compound and which is stably dispersed in an aqueous solution are prepared by two methods. The thus prepared monolayer TMDs were proven to exhibit excellent and sustained antioxidant effects and excellent stability to light and heat.

14 Claims, 24 Drawing Sheets

FUNCTIONALIZED TRANSITION METAL DICHALCOGENIDES AND COMPOSITION FOR ANTIOXIDATION CONTAINING THE SAME

CROSS-REFERENCE TO RELATED APPLICATION

This application claims the priority of Korean Patent Application No. 10-2017-0053805, filed on Apr. 26, 2017, and all the benefits accruing therefrom under 35 U.S.C. § 119, the contents of which in its entirety are herein incorporated by reference.

BACKGROUND

1. Field

The present disclosure relates to functionalized transition metal dichalcogenides, a method for preparing the same and a composition for antioxidation using the same.

2. Description of the Related Art

Transition metal dichalcogenide (TMD) is a compound abundant in the nature. It has a lamellar structure where the MX2 (M: transition metal, X: chalcogen element) unit is stacked on top of each other. TMD has a layered structure like the well-known structure of graphite. Since it has a week bond between the layers, it can be obtained in the form of a two-dimensional monolayer like that of graphene. A two-dimensional layered material has a larger specific surface area and has more active sites per area than a three-dimensional material. Thus, it has been highly anticipated as a catalyst that can be used for hydrogen production by the electrolysis of water, instead of platinum, etc. TMD has a Gibbs free energy close to zero for hydrogen adsorption, and thus can easily adsorb and desorb hydrogen in hydrogen generation reactions. Recently, the hydrogen generation characteristics varying with the sample structure (face and line structures, etc.) are under active research with a focus on $MoS_2$.

Many interesting physical phenomena resulting from the dimension control of TMD have been reported. Major examples thereof include a phenomenon that the material-specific band gap characteristics (direct or indirect band gap) and band gap size change depending on the thickness, unique optical characteristics occurring as the spin-orbit coupling, which is not considered in a three-dimensional material, becomes important, and a quantum-spin Hall effect.

A TMD compound of a two-dimensional layered structure shows high applicability as semiconductor logic devices and electrochemical catalysts, as well as the various applicability found in researches on graphene. However, there is little research on the application of TMD to a field other than the field of semiconductors and electrochemical catalysts. Also, little is known about the technology of functionalizing exfoliated TMD with a specific material or the technology of stably dispersing monolayer TMDs in a solvent.

SUMMARY

In an aspect, the present disclosure is directed to overcome the limitations of the conventional methods for preparing monolayer transition metal dichalcogenides, prepare monolayer transition metal dichalcogenides with a high yield, and to find new properties of monolayer transition metal dichalcogenides and thereby to apply them to fields where they have not been applied.

In an aspect, the present disclosure provides monolayer transition metal dichalcogenides (TMDs) functionalized with an amphiphilic block polymer compound comprising a hydrophilic block and a hydrophobic block.

In an aspect, the present disclosure provides a composition for antioxidation comprising the functionalized monolayer TMDs.

In an aspect, the present disclosure provides a method for preparing functionalized monolayer TMDs, comprising the processes of: mixing an amphiphilic block polymer compound and TMDs with water; and exfoliating the TMDs during or after the mixing process.

In an aspect, the present disclosure provides a method for preparing functionalized monolayer TMDs, comprising the processes of: dispersing TMDs in an organic solvent; dispersing an amphiphilic block polymer compound in an organic solvent separate from the organic solvent; and mixing the solution in which the TMDs are dispersed and the solution in which the amphiphilic block polymer compound is dispersed, and then mixing water therewith.

DETAILED DESCRIPTION

Figure 1A:
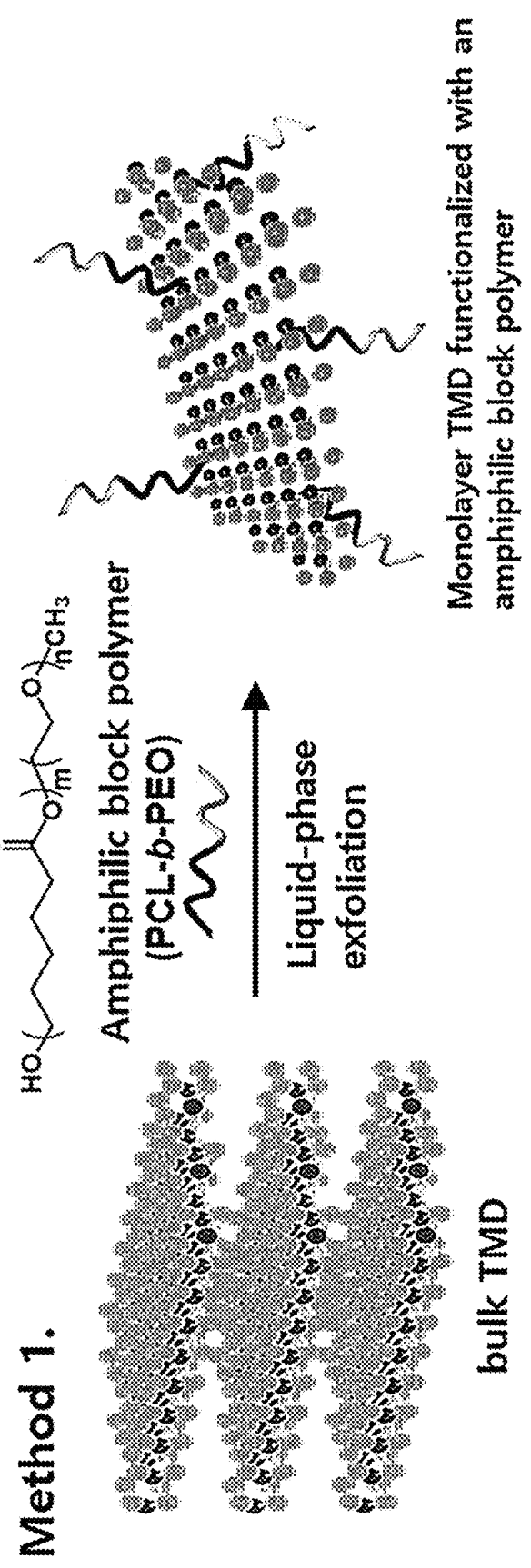
FIG. 1A and FIG. 1B show a schematic diagram of the technology of exfoliating and dispersing transition metal dichalcogenides (TMDs) in an aqueous solution using an amphiphilic block polymer compound.

As used herein, the term "functionalization" covers changing, improving or modifying the physical, chemical, or biological properties (for example, interfacial properties) of an object by introducing, treating with, coating or bonding a physical means (heat, pressure, vibration, light, etc.) or a chemical means (specific compound, polymer, functional group, etc.). For example, introducing a specific polymer compound into an object through hydrophobic interaction may also be a type of functionalization.

As used herein, the term "hydrophilic block" refers to a part of a specific polymer compound having a strong affinity to water. The hydrophilic block is a part which is dispersed in water. According to one aspect of the present invention, a hydrophilic block in an amphiphilic block polymer compound is polyethylene oxide (PEO).

As used herein, the term "hydrophobic block" refers to a part of a specific polymer compound which has no affinity to water and thus which is insoluble in water. According to one aspect of the present invention, a hydrophobic block in an amphiphilic block polymer compound is poly(epsilon-caprolactone) (PCL).

As used herein, the term "amphiphilic block polymer compound" refers to a polymer compound or copolymer containing both a hydrophilic part (block) and a hydrophobic part (block). For example, it may be a block polymer compound or block copolymer ("PCL-b-PEO") containing PEO as a hydrophilic block and PCL as a hydrophobic block.

As used herein, the term "phase transition" refers to a phenomenon in which a phase changes to another phase due to a change in conditions such as temperature, pressure, composition, and mixing with a specific material. As used herein, the term "phase transition method" refers to a method of obtaining functionalized TMDs according to one aspect of the present invention by using a phase transition phenomenon and may include the method according to Example 3.

As used herein, the term "emulsion" refers to a system consisting of two liquids that are immiscible or have a very low miscibility in each other. An emulsion is a metastable system when viewed from a thermodynamic point of view. Thus, it is necessary to add a material having surface activity to maintain the dispersed state of an emulsion. A material used for this purpose and which has surface activity is referred to as an emulsifier. The emulsifier is generally an amphiphilic material having both a hydrophilic part and a lipophilic part. The molecules of the two properties are phase-separated from each other and are oriented toward different phases, respectively, at the interface of oil and water, thus lowering the surface tension. The emulsifier used for the above purpose is classified into an ionic surfactant and a nonionic surfactant based on the type of the hydrophilic group in the molecule. An ionic surfactant is classified into an anionic surfactant, a cationic surfactant and an amphoteric surfactant.

As used herein, "polycaprolactone" refers to a linear polymer having the formula $(CH_2CH_2CH_2CH_2CH_2COO)m$- wherein m is a positive integer. It is widely used as a biodegradable and biocompatible polymer and is a water-insoluble hydrophobic polymer. The molecular weight of the polycaprolactone suitable for forming an amphiphilic block polymer compound according to one aspect of the present invention may vary depending on the structure and molecular weight of the hydrophilic polymer. Generally, the molecular weight is preferably 300 to 60,000 daltons.

As used herein, the term "polyethylene oxide" refers to a polymer having the formula $(CH_2CH_2O)n$- wherein n is a positive integer and which is hydrophilic. Polyethylene oxide is widely used as a medical polymer due to its excellent biocompatibility. It is used in an amphiphilic block polymer compound according to one aspect of the present invention to improve its phase stability. The molecular weight of the polyethylene oxide is determined based on the molecular weight of the polycaprolactone, etc. Generally, it is preferable to use a polyethylene oxide having a weight average molecular weight of 200 to 50,000 daltons, because it is highly likely to form a core-shell type polymer micelle if the molecular weight of the polyethylene oxide is too large.

Transition metal dichalcogenide (TMD) is a compound abundant in the nature. It has a lamellar structure where the $MX_2$ (M: transition metal, X: chalcogen element) unit is stacked on top of each other. TMD can have semiconducting properties and metallic properties depending on the exfoliation method. Thus, it is a new material that can be highly utilized in various fields. Particularly, exfoliated monolayer TMDs having semiconducting properties exert an effect not obtained by bulk TMDs.

The methods for synthesizing semiconducting monolayer TMDs include a chemical vapor deposition method in which a precursor is heated to synthesize a material in the vapor phase, and a mechanical exfoliation method in which bulk TMDs are exfoliated by a physical force. The chemical vapor deposition method is a method of depositing a gaseous raw material on a substrate surface to synthesize monolayer TMDs. It allows to synthesize monolayer TMDs having a relatively large area. The mechanical exfoliation method is a method of exfoliating monolayer TMDs of a lamellar structure formed by Van der Waals force, by applying a physical force. Exfoliation may be performed by a ball milling method using a frictional force. Otherwise, it is possible to exfoliate monolayer TMDs by using an adhesive tape. TMDs with a different degree of exfoliation can be obtained by adjusting the ball milling treatment time or the number of times of exfoliation using an adhesive tape.

The chemical vapor deposition method is an expensive synthesis method in which the reaction proceeds at an ultra-high temperature and thus which involves a lot of energy consumption. It has difficulty in mass production and thus its use is limited. The mechanical exfoliation method has problems that it is difficult to mass-produce monolayer TMDs, the synthesis yield of monolayer TMDs is low, and it is difficult to separate the TMDs which were not exfoliated. When an organic solvent is used in this method, it is difficult to remove the organic solvent. Thus, it cannot have various applications. It has a very low yield of exfoliated monolayer TMDs, and the exfoliated monolayer TMDs have a poor dispersion stability. Particularly, when this method is applied to cosmetic materials, nanomedicine materials, nano-bio materials, biosensor materials, electronic materials, etc., it requires substitution or removal with an aqueous solution, which makes it bothersome, and furthermore, the dispersion stability rapidly decreases during the process. In addition, TMDs exfoliated in an organic solvent have very poor fluorescence properties. Thus, there is an urgent need for a new technology capable of stably dispersing monolayer TMDs in a biocompatible/environment-friendly aqueous solution. One aspect of the present invention provides a solution to these problems.

In one aspect, the present invention provides monolayer transition metal dichalcogenides (TMDs) functionalized with an amphiphilic block polymer compound containing a hydrophilic block and a hydrophobic block.

In one embodiment, the hydrophilic block may be polyethylene oxide (PEO).

In another embodiment, the hydrophobic block may be poly(epsilon-caprolactone) (PCL).

In another embodiment, the amphiphilic block polymer compound may contain PEO and PCL, and may have the structural formula of the following Formula 1:

[Formula 1]

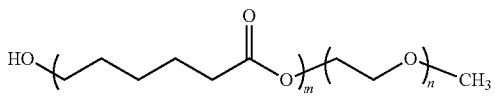

wherein m is an integer of 2 to 70 and n is an integer of 100 to 150.

In one aspect, m may be an integer of 2 or more, 5 or more, 8 or more, 10 or more, 20 or more, 30 or more, 40 or more, 50 or more, 55 or more, 60 or more, or 65 or more. In another aspect, m may be an integer of 70 or less, an integer of 65 or less, an integer of 60 or less, an integer of 58 or less, an integer of 55 or less, an integer of 50 or less, an integer of 45 or less, an integer of 40 or less, an integer of 30 or less, an integer of 20 or less, an integer of 10 or less, an integer of 8 or less, an integer of 5 or less, or an integer of 3 or less. Preferably, m may be an integer of 5 to 55.

In one aspect, n is an integer of 100 or more, an integer of 105 or more, an integer of 110 or more, an integer of 115 or more, an integer of 120 or more, an integer of 122 or more, an integer of 124 or more, an integer of 125 or more, an integer of 130 or more, an integer of 135 or more, an integer of 140 or more, or an integer of 145 or more. In another aspect, n may be an integer of 150 or less, an integer of 145 or less, an integer of 140 or less, an integer of 135 or less, an integer of 130 or less, an integer of 125 or less, an integer of 124 or less, an integer of 120 or less, an integer of 115 or less, an integer of 110 or less, an integer of 105 or less, or an integer of 103 or less. Preferably, n may be 124.

In another embodiment, the amphiphilic block polymer compound may have a weight average molecular weight of 3000 to 20,000 and have a weight ratio of PCL:PEO of 1:0.5 to 1:20.

In one aspect, the amphiphilic block polymer compound may have a weight average molecular weight of 3000 or more, 4000 or more, 5000 or more, 5500 or more, 6000 or more, 7000 or more, 8000 or more, 9000 or more, 10000 or more, 11000 or more, 12000 or more, 15000 or more, or 18000 or more. In another aspect, the amphiphilic block polymer compound may have a weight average molecular weight of 20000 or less, 18000 or less, 15000 or less, 12000 or less, 10000 or less, 8000 or less, 6000 or less, 5500 or less, 5000 or less, 4000 or less, or 3500 or less. Preferably, the amphiphilic block polymer compound may have a weight average molecular weight of 5500 to 10000.

In one aspect, the weight ratio of PCL:PEO may be 1:0.5 or more, 1:0.7 or more, 1:0.9 or more, 1:1 or more, 1:2 or more, 1:5 or more, 1:8 or more, 1:10 or more, 1:12 or more, 1:14 or more, 1:16 or more, or 1:18 or more. In another aspect, the weight ratio of PCL:PEO may be 1:20 or less, 1:18 or less, 1:16 or less, 1:14 or less, 1:12 or less, 1:10 or less, 1:9 or less, 1:8 or less, 1:5 or less, 1:3 or less, 1:2 or less, 1:1 or less, 1:0.8 or less, or 1:0.6 or less. Preferably, the weight ratio of PCL:PEO may be 1:1 to 1:10.

In addition, in one aspect, the PCL may have a molecular weight of 200 to 7000, and the PEO may have a molecular weight of 4000 to 6000. The preferable molecular weight of the PCL may be 500 to 5000, and the preferable molecular weight of the PEO may be 5000.

In one embodiment, the polyethylene oxide and the polycaprolactone in the amphiphilic block polymer compound (copolymer) consisting of a polycaprolactone as a hydrophobic block and a polyethylene oxide as a hydrophilic block may be covalently bonded to each other.

In another embodiment, the TMDs may be one or more selected from the group consisting of molybdenum disulfide ($MoS_2$), tungsten disulfide ($WS_2$), molybdenum diselenide ($MoSe_2$), and tungsten diselenide ($WSe_2$).

In another embodiment, the functionalized monolayer TMDs may have a thickness of 1 to 10 nm. In one aspect, the thickness may be 1 nm or more, 2 nm or more, 3 nm or more, 4 nm or more, 5 nm or more, 6 nm or more, 7 nm or more, 8 nm or more, or 9 nm or more. In another aspect, the thickness may be 10 nm or less, 9 nm or less, 8 nm or less, 7 nm or less, 6 nm or less, 5 nm or less, 4 nm or less, 3 nm or less, or 2 nm or less.

In another embodiment, the TMDs may be a monolayer. In one aspect, the TMDs may be a bilayer or a trilayer.

In one aspect, the functionalized monolayer TMDs may be dispersed in a medium. In another aspect, the present invention may relate to a dispersion in which the functionalized monolayer TMDs are dispersed.

In one embodiment, the medium may be an aqueous solution or an oil-in-water (O/W) emulsion. In addition, the formulation of the dispersion may be an aqueous solution or an oil-in-water (O/W) emulsion.

In another aspect, the present invention may relate to a composition for antioxidation containing the functionalized monolayer TMDs or the dispersion. The functionalized TMDs have antioxidant activity. Thus, in one aspect, the present invention can be sufficiently applied to the technology of synthesizing an antioxidant based on transition metal dichalcogenide compounds, cosmetic material technology, e-cosmetics technology, the technology of functionalizing transition metal dichalcogenides in an aqueous solution, etc.

In one embodiment, the composition may be an agent for external application to the skin or a cosmetic composition.

There is no particular limitation on the formulation of the agent for external application to the skin or the cosmetic composition. However, they can be formulated into various forms that can be applied to skin, mucous membrane, scalp, body hair including head hair, nail, and mouth, for example, a composition selected from a softening lotion, a nourishing lotion, a lotion, a cream, a pack, a gel, a patch, a spray or a mist, a coloring composition selected from a lipstick, a makeup base or a foundation, a composition selected from a shampoo, a hair conditioner, a body cleanser, a toothpaste, or a mouthwash, and a hair care composition selected from a hair fixative such as a hair tonic, a gel, and a mousse, a hair growth promoter, or a hairdye. Also, it can be utilized in various forms such as a lotion, an ointment, a gel, a cream, a pack, a mist or a spray. When it is used as an agent for external application to the skin, the applicable product groups include cosmetics, medicines and quasi-drugs, without particular limitations.

The composition may further contain a surfactant, an emulsifier, an excipient, a suspending agent, a coloring agent, a flavoring agent, an oil, a wax, a polyol and other additives commonly used in cosmetic compositions, etc., without particular limitations.

In another aspect, the present invention may relate to a method for preparing the functionalized monolayer TMDs, comprising the process of combining an amphiphilic block polymer compound and TMDs with water.

In one embodiment, the method may further comprise the process of exfoliating TMDs during or after the mixing process.

In another embodiment, the exfoliation may be performed ultrasonically.

Bulk TMDs were ultrasonically exfoliated in an aqueous solution using an amphiphilic block polymer compound (PCL-b-PEO), according to the method, to synthesize monolayer TMDs functionalized with an amphiphilic block polymer compound. The thus synthesized TMDs exhibited excellent and sustained antioxidant activity and showed excellent dispersion stability and antioxidant activity stability against light and heat. The thus functionalized TMDs were encapsulated by a hydrogel to prepare a cosmetic composition.

The use of an organic solvent may cause problems such as toxicity, environmental pollution, limitation in application to humans, etc. However, the present disclosure solved the problems by proposing a new liquid-phase exfoliation method of effectively exfoliating and stably dispersing monolayer TMDs in an aqueous solution by using a biocompatible amphiphilic block polymer compound.

In another aspect, the present invention may relate to a method for preparing the functionalized monolayer TMDs, comprising the processes of: dispersing TMDs in an organic solvent; dispersing an amphiphilic block polymer compound in an organic solvent separate from the organic solvent; and mixing the solution in which the TMDs are dispersed and the solution in which the amphiphilic block polymer compound is dispersed and then mixing water therewith.

In one embodiment, the preparation method may further comprise the process of exfoliating the TMDs during or after the process of dispersing the TMDs. In another embodiment, the preparation method may further comprise the process of exfoliating the TMDs during or after the process of mixing the solution in which the TMDs are dispersed and the solution in which the amphiphilic block polymer compound is dispersed and then mixing water therewith.

In another embodiment, the process of mixing water may be the process of causing phase transition by instilling and mixing water.

In another embodiment, the organic solvent for dispersing the TMDs or the organic solvent for dispersing the amphiphilic block polymer compound may be one or more selected from the group consisting of an aprotic solvent (solvent which does not donate a proton), a C1 to C5 alcohol, a C1 to C5 ketone, and mixtures thereof. The aprotic solvent may be polar or non-polar.

In another embodiment, the organic solvent for dispersing the TMDs or the organic solvent for dispersing the amphiphilic block polymer compound may be one or more selected from the group consisting of N-methylpyrrolidone, tetrahydrofuran, ethanol, methanol, dichloromethane, dimethyl sulfoxide, acetone, and mixtures thereof. The type and amount of the organic solvent are not particularly limited and may be such that the polymer can be uniformly dispersed.

In another embodiment, the method may further comprise the process of removing the organic solvent for dispersing the TMDs or the organic solvent for dispersing the amphiphilic block polymer compound after the process of mixing water. The removal may be performed by methods such as evaporation under reduced pressure, dialysis, and extraction.

Monolayer TMDs functionalized with an amphiphilic block polymer compound was obtained in an aqueous solution through a method of using a phase transition phenomenon (phase transition method) on monolayer TMDs exfoliated in an organic solvent. Also, functionalized monolayer TMDs were obtained in an aqueous solution by removing the organic solvent through evaporation under reduced pressure or dialysis. It was found that monolayer TMDs were functionalized in an aqueous solution by the hydrophobic interaction with an amphiphilic block polymer compound and that the resultant had excellent and sustained dispersion stability.

The technology of exfoliating, functionalizing and dispersing monolayer TMDs using an amphiphilic polymer according to one aspect of the present invention can be applied to various types of TMDs ($MoS_2$, $MoSe_2$, $WS_2$, $WSe_2$, etc.). Besides, it can be used for exfoliation and functionalization of other types of materials of a layered structure. The monolayer TMDs functionalized with an amphiphilic block polymer exhibited very excellent antioxidant effects. Also, even after long-term storage and changes in light and heat, they showed the same antioxidant activity as the initial state. These antioxidant effects of monolayer TMDs are new effects that have not been reported before.

Hereinafter, the constitution and effects of one aspect of the present invention will be described in more detail through examples, test examples, etc. However, the following examples are provided for illustrative purposes only to facilitate understanding of the present invention, and the scope of the present invention are not limited thereto.

EXAMPLE 1

Preparation of an Amphiphilic Block Polymer Compound (PCL-b-PEO)

The amphiphilic block polymer compound (amphiphilic copolymer) of the present invention was prepared by the ring-opening polymerization of caprolactone monomers. A fixed quantity of hydrophilic polymer (polyethylene oxide (PEO)) and stannous octoate ($Sn(Oct)_2$) (Sigma, St. Louis, Mo., USA) as a catalyst were put in a glass flask containing hexamethyldisilazine silanized by reaction with the hydroxyl group. Then, caprolactone monomers were introduced and uniformly mixed. The flask containing the mixture was subjected to removal of moisture, etc. under vacuum and then sealed. Then, polymerization was performed at 120° C. After 24 hours, the polymerized polymer was dispersed in methylene chloride and recrystallized with excess methanol to obtain a pure amphiphilic block polymer compound (PCL-b-PEO).

The amphiphilic block polymer compound has the following structural formula:

[Formula 1]

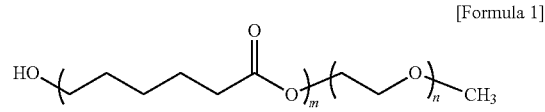

From a structural analysis, a mass analysis, etc., it was found that, in the above formula, m may be an integer of 2 to 70, and that n may be an integer of 100 to 150. However, it was found that m and n may be, independently, various integers within the above numerical range according to the preparation conditions, etc.

The weight average molecular weight of the thus obtained amphiphilic polymer compound was analyzed by gel permeation chromatography (GPC). The GPC system used in the test was an Agilent 110 series (Agilent Technologies, Palo Alto, Calif., USA). Polymer was detected by a refractive index (RI) detector, and three PLgel columns (300×7.5 mm, pore size=$10^3$, $10^4$ and $10^5$ Å) were used. The flow rate was 1.0 milliliter/minute. Tetrahydrofuran (THF) was used as the mobile phase.

It was found that the weight ratio of PCL:PEO in the PCL-b-PEO block copolymer according to one aspect of the present invention may range from 1:0.5 to 1:20, preferably from 1:1 to 1:10. Also, it was found that the weight average molecular weight of the synthesized PCL-b-PEO may range from about 5500 to 20,000, preferably from 5,500 to 10,000.

EXAMPLE 2

Functionalization of TMDs and Dispersion Thereof in an Aqueous Solution

PCL-b-PEO, an amphiphilic block polymer compound, was dispersed in 20 mL of distilled water with heating, and then mixed with 2.4 mmol of TMDs. The resultant mixture was subjected to the process of exfoliation and dispersion using an ultrasonicator for 1 hour and then centrifuged. Bulk TMDs (any commercially available one can be used) which were not exfoliated by the process and too small TMD pieces were removed to obtain monolayer TMDs functionalized with an amphiphilic block polymer compound. In addition, it was found that it was possible to change the monolayer to a bilayer or a trilayer by controlling the RPM and time of the centrifugation.

Monolayer disulfide molybdenum ($MoS_2$), tungsten disulfide ($WS_2$), molybdenum diselenide ($MoSe_2$), and tungsten diselenide ($WSe_2$) functionalized with an amphiphilic block polymer compound were synthesized by the above method. Method 1 of FIG. 1A shows a schematic diagram of the process. Monolayer TMDs functionalized with a block polymer compound were obtained by the technology of aqueous phase exfoliation using an amphiphilic block polymer compound.

TEST EXAMPLE 1

Comparison with the Case Where an Amphiphilic Block Polymer Compound is Not Used It was tested whether the TMDs functionalized and dispersed according to Example 2 had a high exfoliation efficiency and formed a stable dispersion in an aqueous solution.

Specifically, the exfoliation efficiency and stability were compared between the aqueous solution containing bulk TMDs ($MoS_2$, $WS_2$, $MoSe_2$, and $WSe_2$) exfoliated without an amphiphilic block polymer compound and the monolayer TMDs prepared according to Example 2.

Figure 2A:
FIG. 2A and FIG. 2B show photographs of an aqueous solution containing TMDs exfoliated without an amphiphilic block polymer compound and an aqueous solution in which TMDs exfoliated using an amphiphilic block polymer compound are dispersed.
Figure 2B:
Figure 3A:
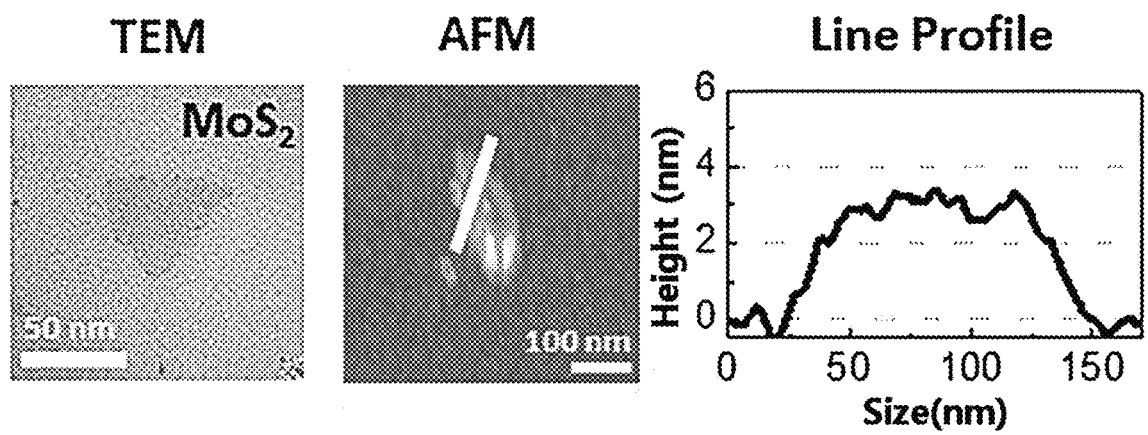
FIG. 3A to FIG. 3D show transmission electron microscope (TEM) photographs and atomic force microscope (AFM) photographs of monolayer TMDs functionalized with an amphiphilic block polymer compound.
Figure 3B:
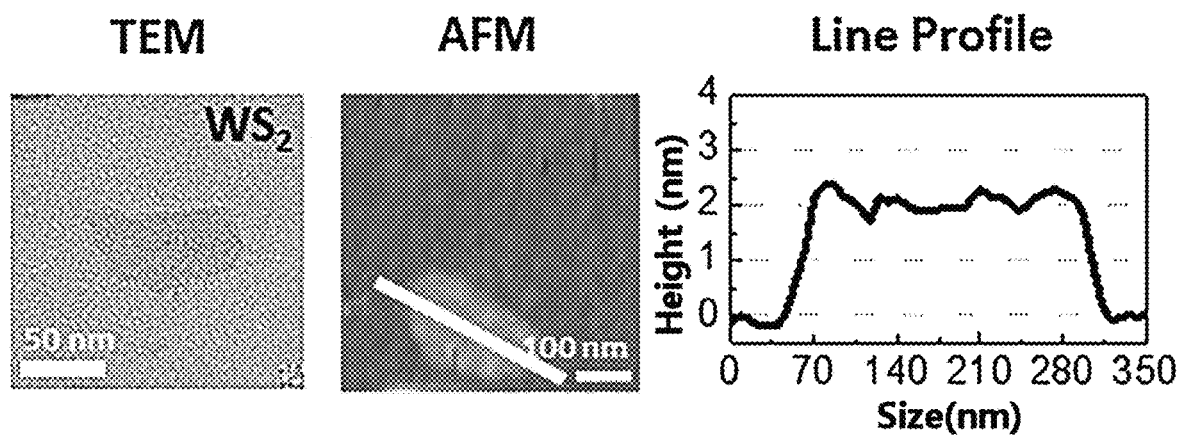
Figure 3C:
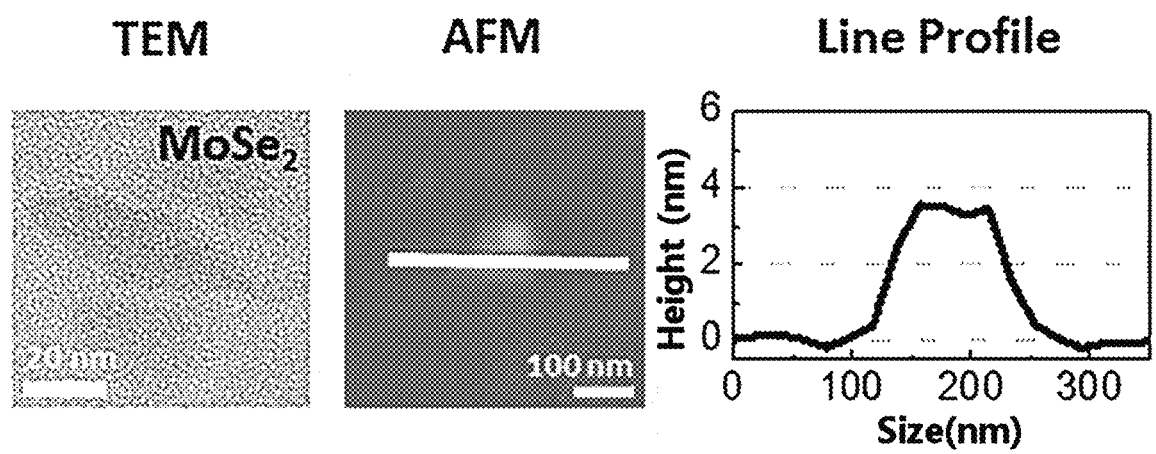
Figure 3D:
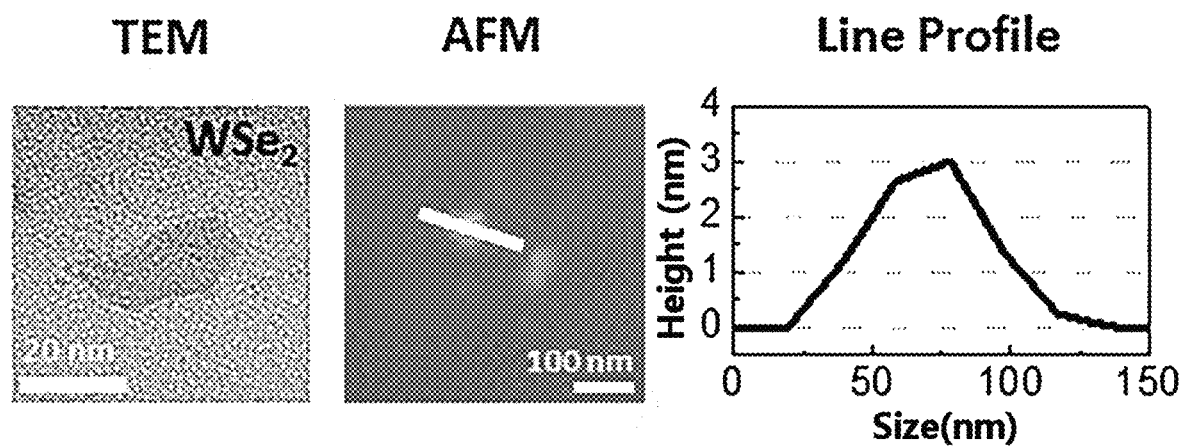

As a result, as shown in FIG. 2A and FIG. 2B, it was found that the case (FIG. 2B) of using an amphiphilic block polymer compound achieved a much higher (38 to 254.9 times higher; see FIG. 5B) monolayer TMDs exfoliation efficiency and dispersion stability than the case (FIG. 2A) of not using it (FIG. 2A shows the aggregation of TMDs to form crystals or agglomerates without proper dispersion, and FIG. 2B shows the uniform dispersion of TMDs).

TEST EXAMPLE 2

Structural Analysis, Optical Properties Analysis and Yield Analysis of Monolayer TMDs Functionalized with an Amphiphilic Block Polymer Compound A structural analysis was carried out for monolayer TMDs functionalized with an amphiphilic block polymer compound, using a transmission electron microscope and an atomic force microscope (FIG. 3A to FIG. 3D).

FIG. 3A to FIG. 3D show transmission electron microscope (TEM) photographs of $MoS_2$, $WS_2$, $MoSe_2$ and $WSe_2$ exfoliated and dispersed in an aqueous solution, and atomic force microscope (AFM) photographs of monolayer TMDs functionalized with an amphiphilic block polymer compound. As seen from the drawings, it was found that the TMDs functionalized with an amphiphilic block polymer compound were well exfoliated to an average size of 50 to 150 nm. From AFM, it was found that $MoS_2$, $WS_2$, $MoSe_2$ and $WSe_2$ exfoliated and functionalized in an aqueous solution had a thickness of 2 to 4 nm, which indicates that the monolayer TMDs were functionalized with an amphiphilic block polymer compound.

In addition, $MoS_2$, $WS_2$, $MoSe_2$ and $WSe_2$ exfoliated and functionalized in an aqueous solution were analyzed for the intrinsic fluorescence properties. That is, the optical properties (fluorescence, absorbance and Raman scattering) of monolayer TMDs functionalized with an amphiphilic block polymer compound were plotted in FIG. 4, FIG. 5A and FIG. 5B, and FIG. 6A to FIG. 6D, respectively.

Figure 4:
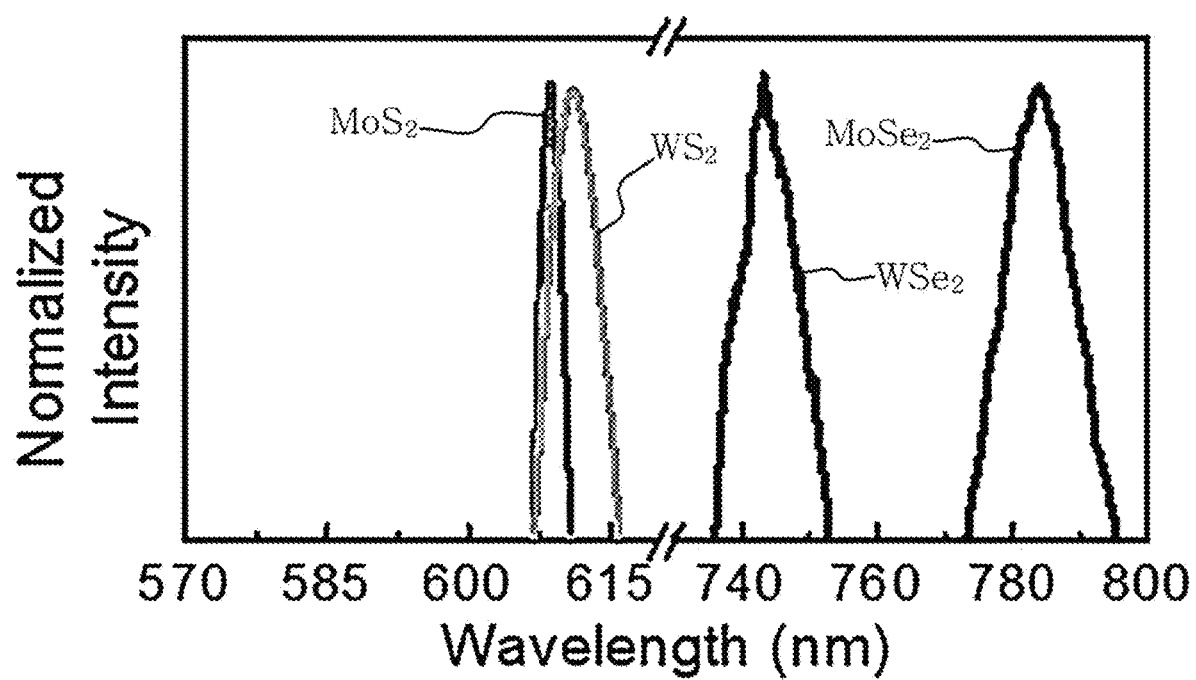
FIG. 4 shows the fluorescence properties of monolayer TMDs functionalized with an amphiphilic block polymer compound.

FIG. 4 shows the fluorescence properties of monolayer TMDs functionalized with an amphiphilic block polymer compound. From FIG. 4, it was found that the fluorescence wavelength of monolayer TMDs exfoliated and functionalized in an aqueous solution was consistent with known values ($MoS_2$: 1.8 to 2.1 eV, $WS_2$: 1.8 to 2.1 eV, $MoSe_2$: 1.4 to 1.7 eV, $WSe_2$: 1.5 to 1.7 eV), indicating that the monolayer TMDs functionalized with an amphiphilic block polymer compound in an aqueous solution showed very strong fluorescence properties in the visible light region.

Figure 5A:
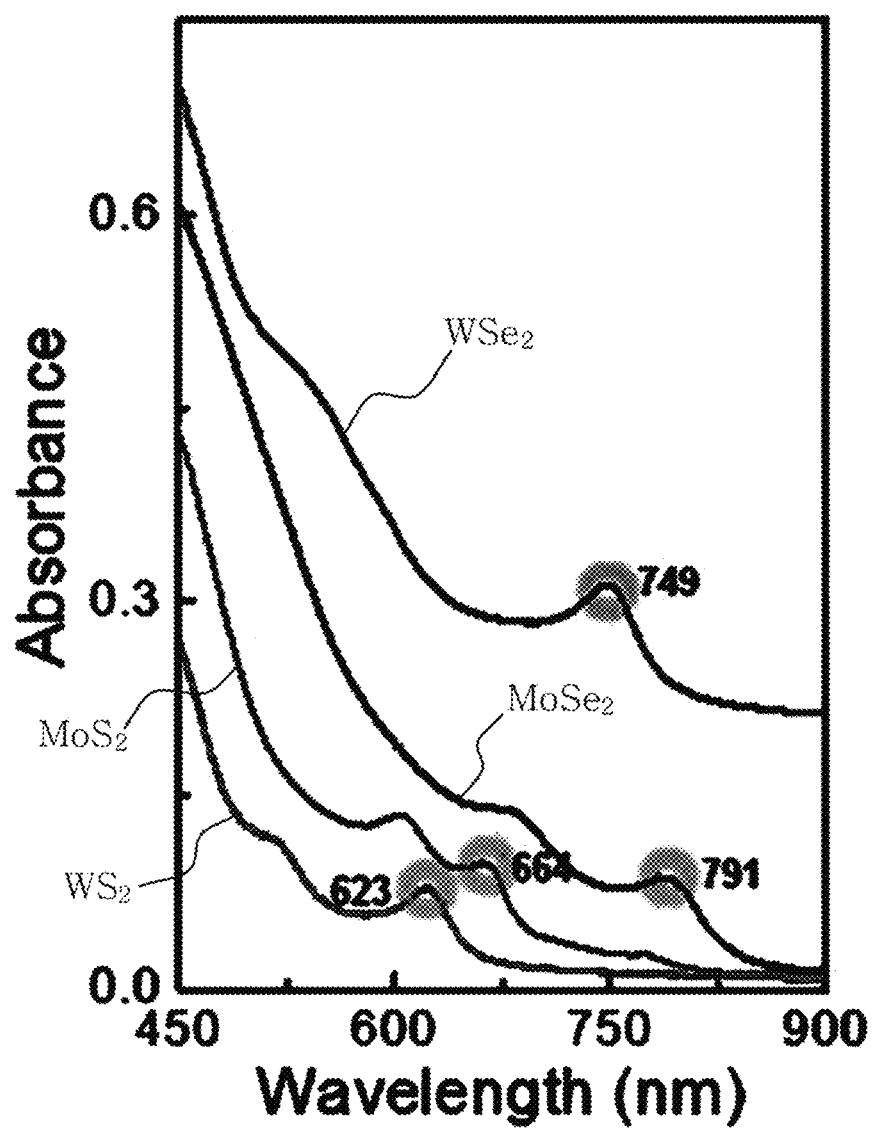
FIG. 5A and FIG. 5B show the absorbance properties and exfoliation yield of monolayer TMDs functionalized with an amphiphilic block polymer compound.
Figure 5B:
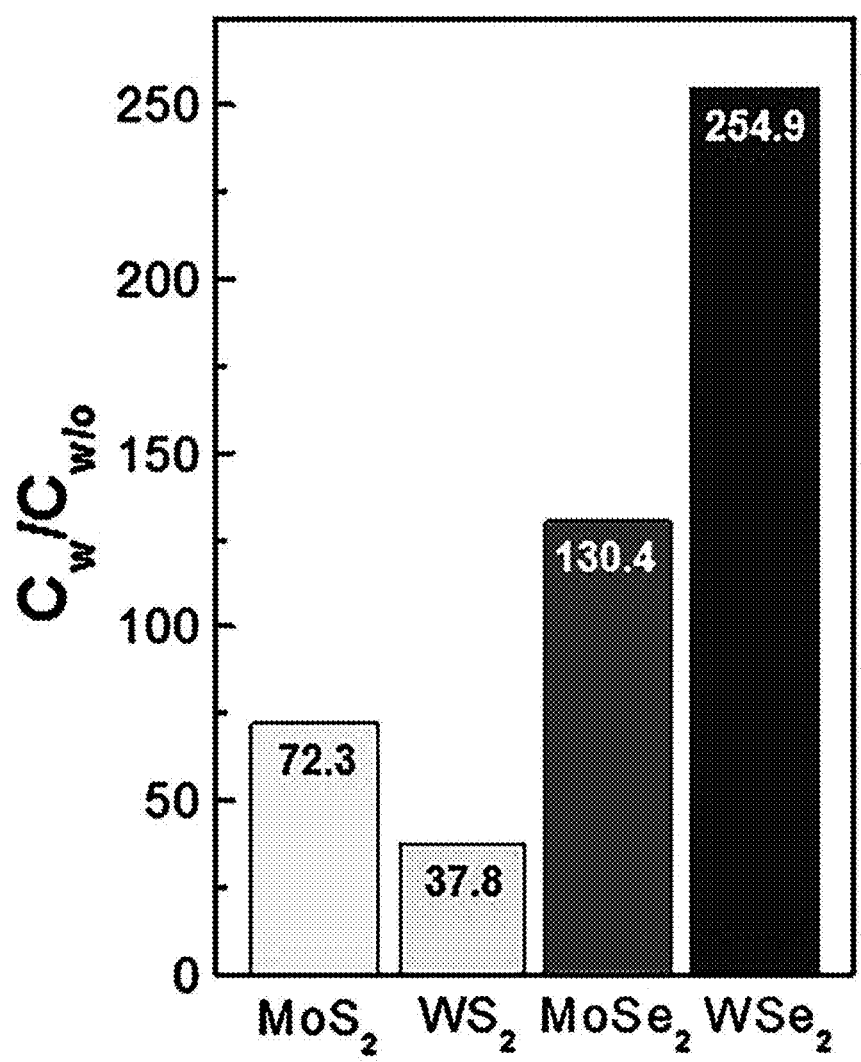

FIG. 5A and FIG. 5B show the absorbance properties (the measurement of exfoliated TMDs was carried out in a 4-mL quartz cell using Mega-2100 (Scinco, Korea)) and the exfoliation yield of monolayer TMDs functionalized with an amphiphilic block polymer compound. FIG. 5($a$) shows the absorbance spectra of $MoS_2$, $WS_2$, $MoSe_2$ and $WSe_2$ functionalized with an amphiphilic block polymer compound in an aqueous solution. FIG. 5A shows the characteristic A-exciton absorption band of monolayer TMDs exfoliated and functionalized (indicated by circle; this absorption band does not appear in bulk TMD, and thus the appearance of this band indicates monolayer TMD). FIG. 5B shows the concentration ratio of TMDs functionalized with an amphiphilic block polymer compound and TMDs exfoliated without an amphiphilic block polymer compound. In light of the fact that absorbance is proportional to concentration (Beer-Lambert law), the yields of the exfoliation in an aqueous solution before and after the use of an amphiphilic block polymer compound were compared based on the absorbance in the A-exciton region. ($C_w$: absorbance of TMDs dispersed using an amphiphilic block polymer compound, $C_{w/o}$: absorbance of TMDs dispersed without an amphiphilic block polymer compound). The results showed that the exfoliation yield increased by about 38 times to about 254.9 times or more depending on the type of TMD.

Figure 6A:
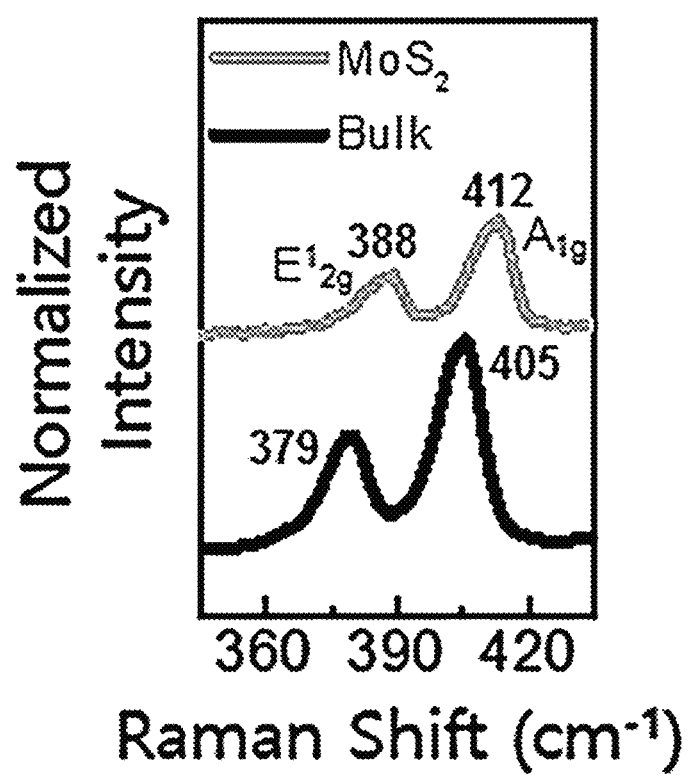
FIG. 6A to FIG. 6D show the Raman scattering properties of monolayer TMDs functionalized with an amphiphilic block polymer compound.
Figure 6B:
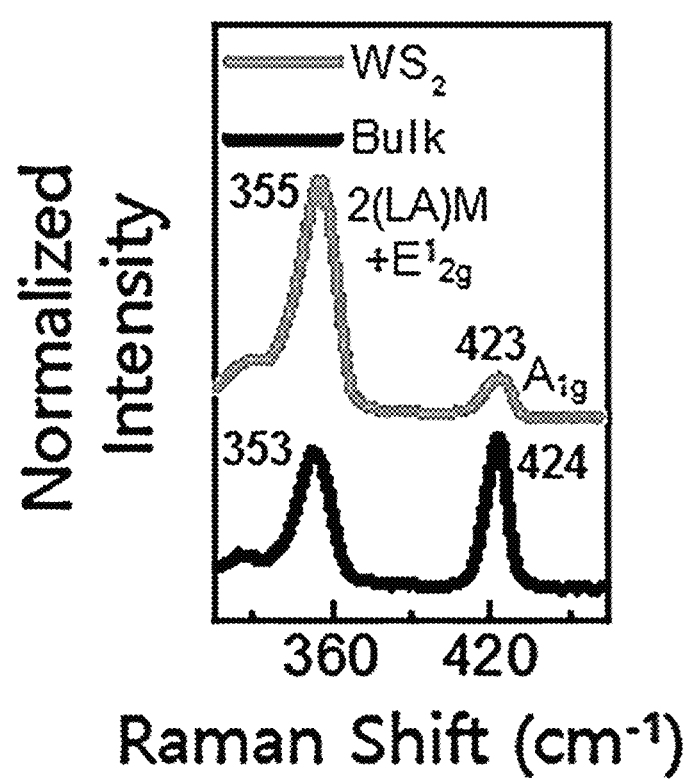
Figure 6C:
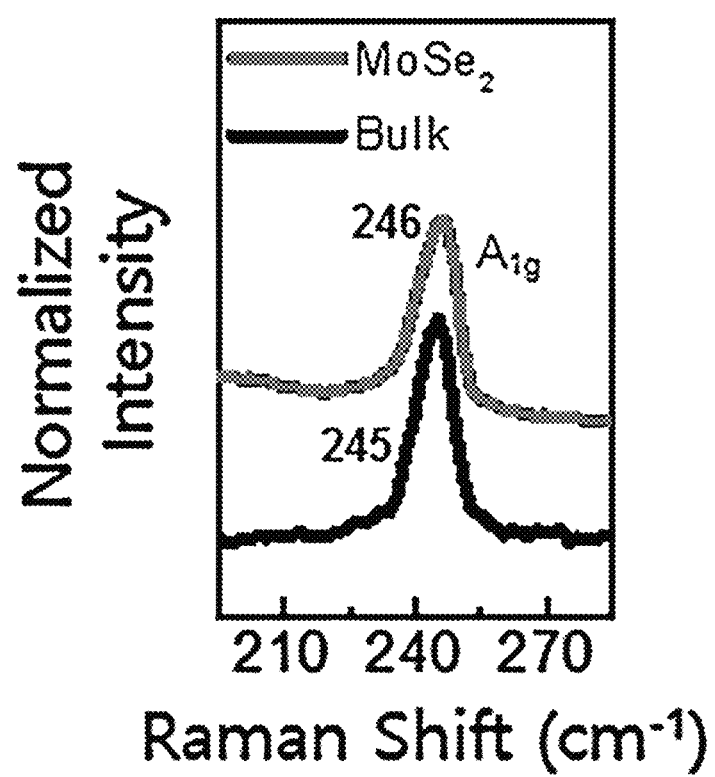
Figure 6D:
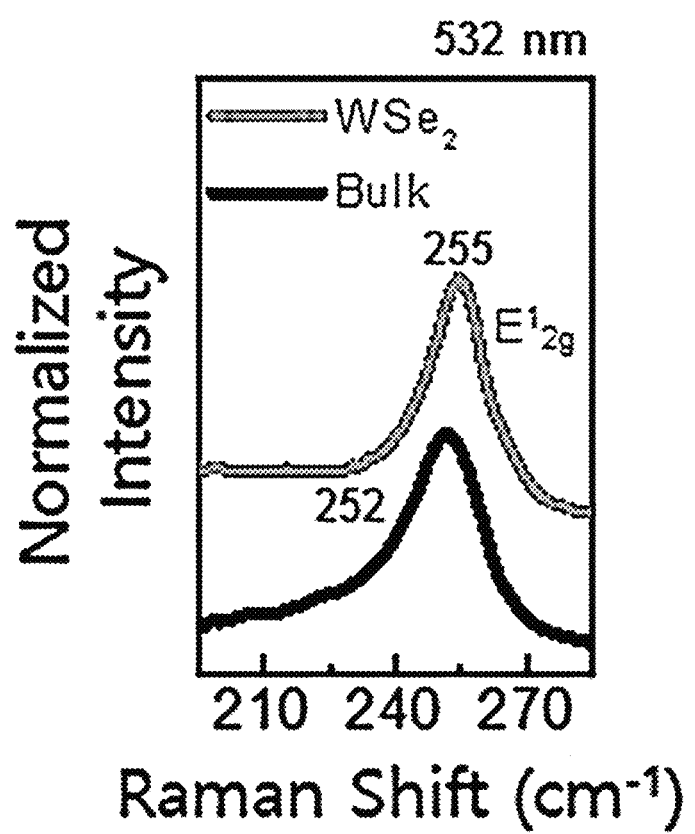

In addition, the Raman scattering properties of monolayer TMDs functionalized with an amphiphilic block polymer compound were tested using UniRAM-193DR (Uninano technology, Korea). Bulk TMDs were placed on a silicon wafer and analyzed using a 532 nm laser at 5 mW. 130 uL of exfoliated TMDs were sampled with a 384-well plate and analyzed using a 532 nm laser at 5 mW. FIG. 6A indicates that the Raman scattering signal of the exfoliated and functionalized monolayer $MoS_2$ showed a blue shift and narrow Raman peak spacing relative to those of bulk $MoS_2$. Also, FIG. 6B indicates that the Raman scattering signal of the exfoliated and functionalized monolayer $WS_2$ showed a decreased out-of-plane vibration mode ($A_{1g}$) peak compared with the Raman scattering signal of bulk $WS_2$. FIG. 6C indicates that the Raman scattering signal of the exfoliated and functionalized monolayer $MoSe_2$ showed almost no change from the Raman scattering signal of bulk $MoSe_2$. FIG. 6D indicates that the Raman scattering signal of the exfoliated and functionalized monolayer $WSe_2$ showed a blue shift relative to the Raman scattering signal of bulk $WSe_2$.

EXAMPLE 3

Figure 7A:
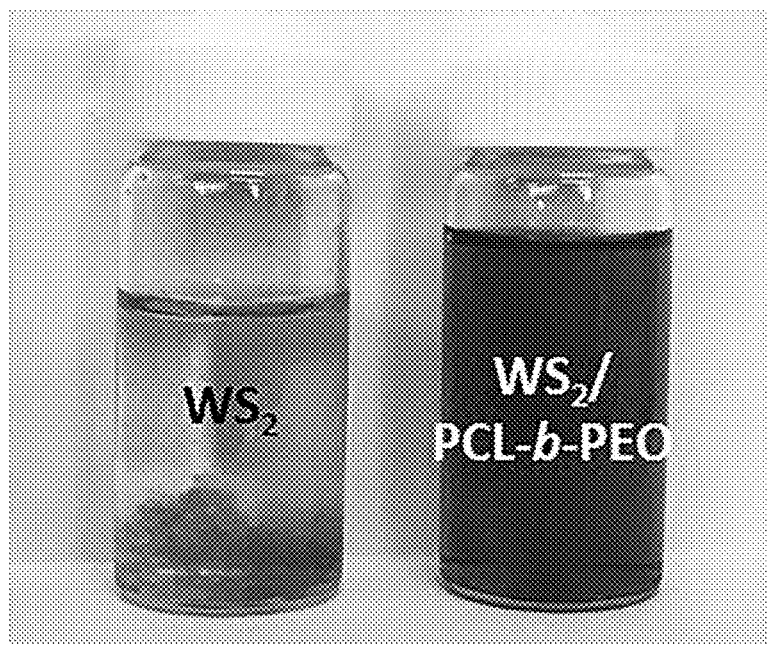
FIG. 7A to FIG. 7C show a photograph of the aqueous solution of the monolayer $WS_2$ functionalized with an amphiphilic block polymer compound according to Example 3 and a TEM image of the monolayer $WS_2$.
Figure 7B:
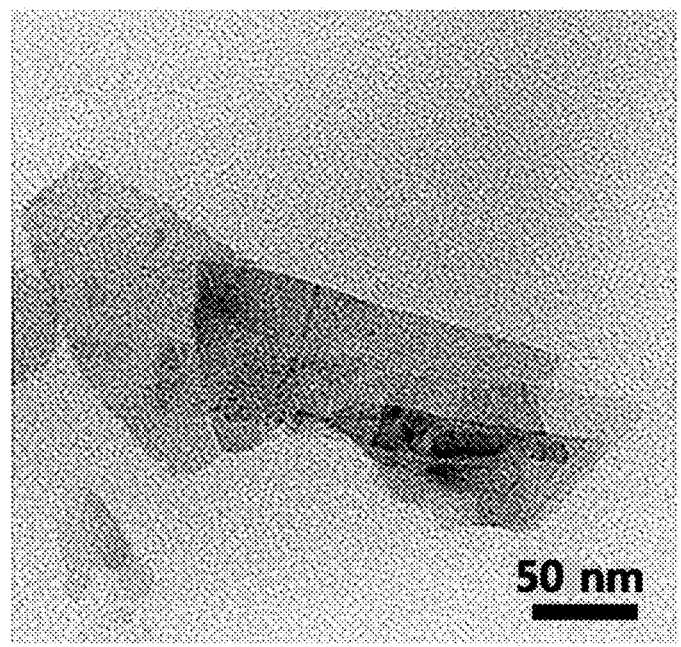
Figure 7C:
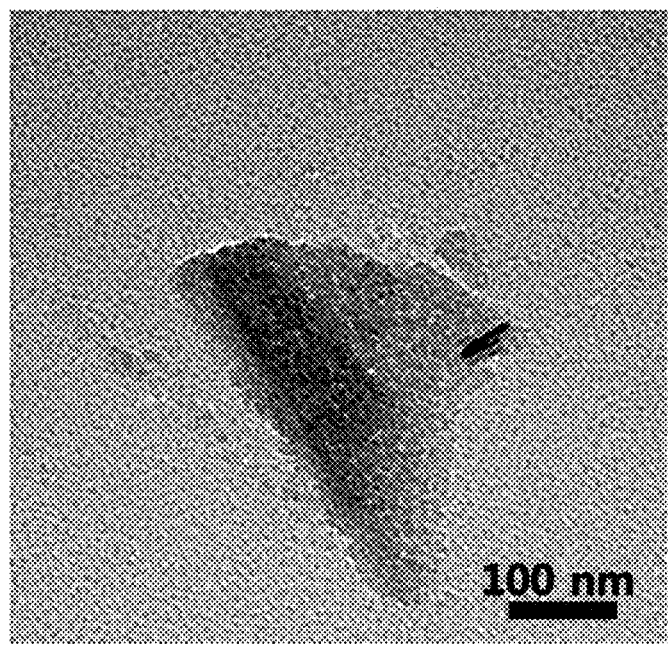
Figure 8A:
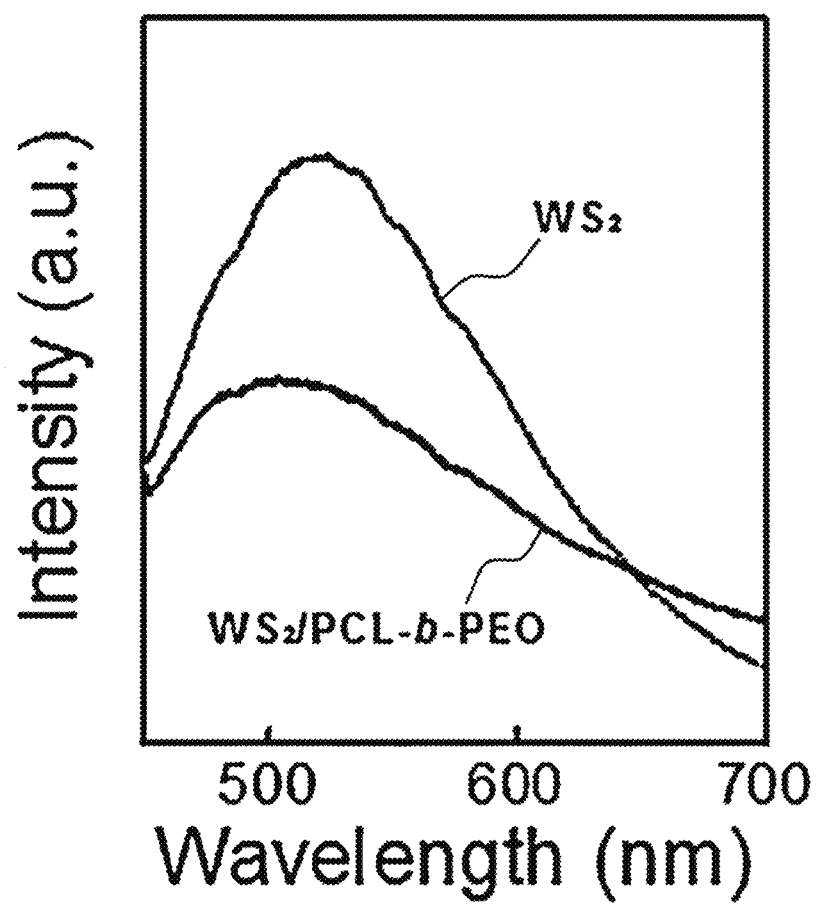
FIG. 8A to FIG. 8C show the optical properties of the monolayer $WS_2$ functionalized with an amphiphilic block polymer compound according to Example 3.
Figure 8B:
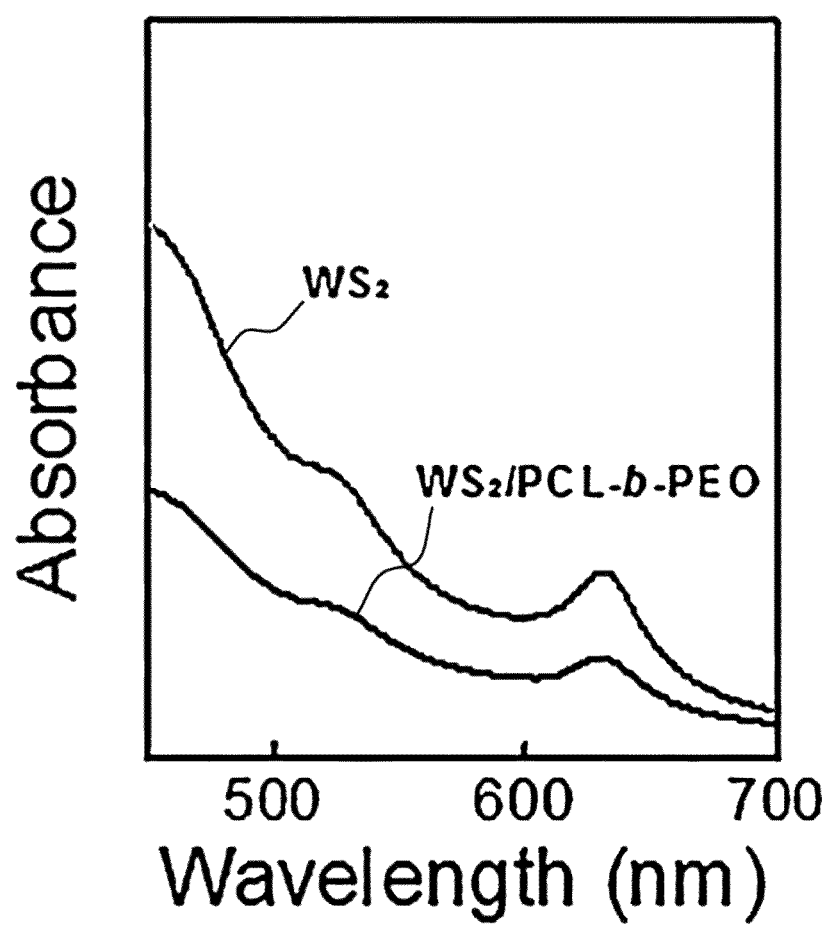
Figure 8C:
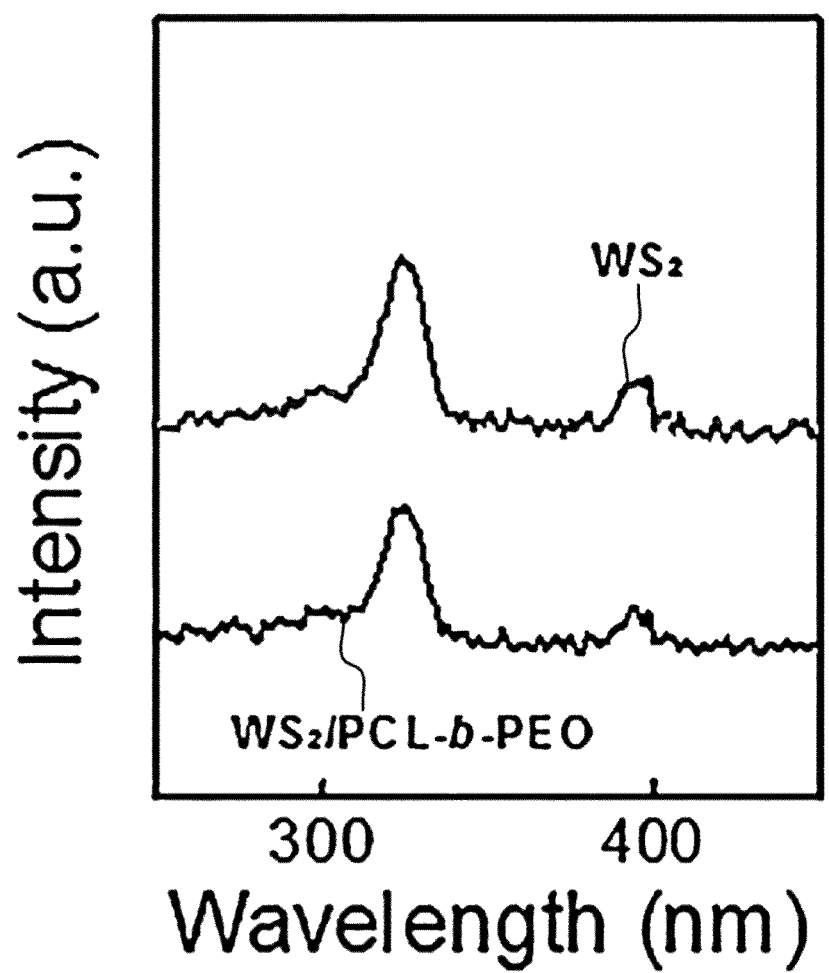

Functionalization and Dispersion in an Aqueous Solution of TMDs Using Phase Transition First, TMDs were dispersed in an organic solvent. Specifically, TMDs were added to 100 mL of N-methylpyrrolidone (NMP) solvent and exfoliated for 1 hour and 30 minutes using an ultrasonicator (commercially available and conventional tip sonicator, 130 W). After ultrasonication, the bulk which was not dispersed was removed by centrifugation (2 times, 1 hour at 700×g/1 hour at 2500×g). The conditions and the number of times of centrifugation may be appropriately adjusted according to the purpose, etc. It was found that tetrahydrofuran, ethanol, methanol, dichloromethane, dimethyl sulfoxide, acetone, or a mixture thereof can be used as the solvent instead of N-methylpyrrolidone. FIG. 7A to FIG. 7C show transmission electron microscope (TEM) images of the exfoliated TMDs. FIG. 8A to FIG. 8C show a graph of their optical properties analyzed through photoluminescence, ultraviolet-visible spectroscopy, and Raman spectroscopy.

Then, TMDs functionalized using phase transition were dispersed in an aqueous solution (phase transition method). Specifically, four types of TMDs ($MoS_2$, $WS_2$, $MoSe_2$, and $WSe_2$) exfoliated in a N-methylpyrrolidone solvent (tetrahydrofuran, ethanol, methanol, dichloromethane, dimethyl sulfoxide, acetone, or a mixture thereof can also be used) were mixed with a solution of tetrahydrofuran (N-methylpyrrolidone solvent, ethanol, methanol, dichloromethane, dimethyl sulfoxide, acetone, or a mixture thereof can also be used) in which an amphiphilic block polymer compound PCL-b-PEO was dispersed. Then, 10 mL of water was slowly instilled at a rate of 100 µL min$^{-1}$ and phase transition was performed at 40° C. Thereafter, the tetrahydrofuran solvent was removed by evaporation under reduced pressure at 45° C. Then, dialysis was performed by adding to a dialysis membrane (1 kD), sealing, and stirring for 3 days with changing water frequently, to remove the N-methylpyrrolidone solvent.

Figure 1B:
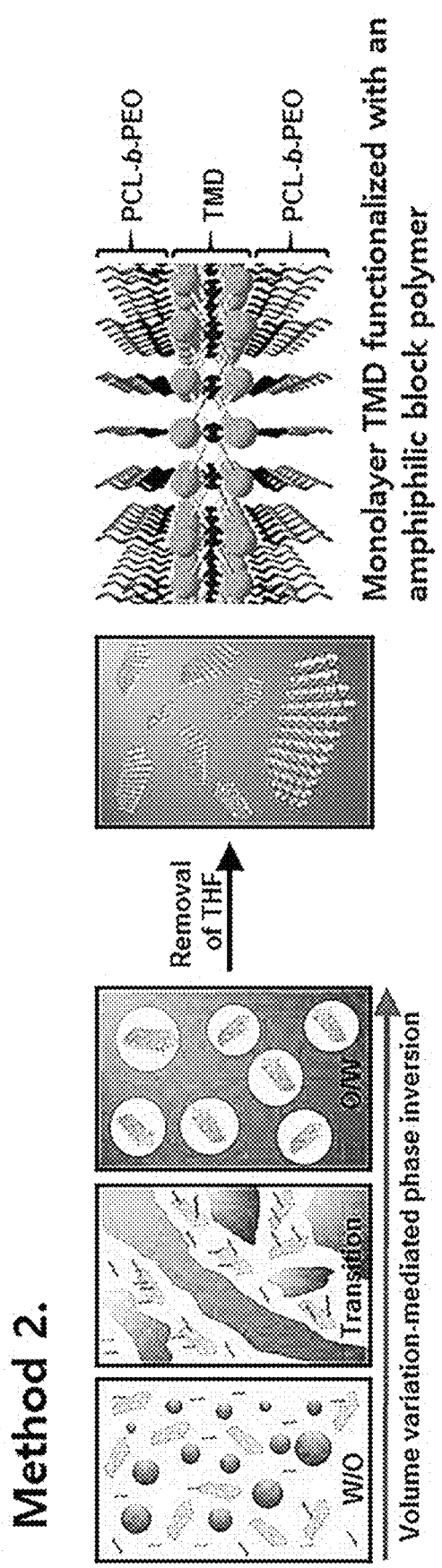

FIG. 1B (Method 2) shows a schematic diagram of the process and an image of encapsulated TMDs. Method 2 of FIG. 1B illustrates the process of functionalizing TMDs dispersed in an organic solvent with an amphiphilic block polymer compound using a phase transition method and dispersing them in water. It was found that the monolayer TMDs functionalized with an amphiphilic block polymer compound were stably dispersed in an aqueous solution while retaining the inherent characteristics of exfoliated TMDs (FIG. 7A).

TEST EXAMPLE 3

Visual Confirmation and Optical Properties Analysis of an Aqueous Solution of Monolayer TMDs Obtained by Using a Phase Transition Method FIG. 7A to FIG. 7C show an image (FIG. 7A) of an aqueous solution of monolayer TMDs functionalized with an amphiphilic block polymer compound using the phase transition method and TEM images (FIG. 7B and FIG. 7C) of the monolayer TMDs. FIG. 7A shows a photograph of an aqueous solution of $WS_2$ exfoliated in an organic solvent and functionalized with an amphiphilic block polymer compound by the phase transition method (right side of FIG. 7A) and a photograph of an aqueous solution of $WS_2$ which was exfoliated in an organic solvent and then directly added to the aqueous solution (left side of FIG. 7A). It was found that the monolayer $WS_2$ functionalized with an amphiphilic block polymer compound using a phase transition method exhibited very excellent dispersion stability in an aqueous solution. In contrast, when a $WS_2$ organic solution was directly added to an aqueous solution without functionalization with an amphiphilic block polymer compound through phase transition, it had a low dispersion stability, resulting in immediate aggregation and precipitation.

FIG. 7B is a TEM photograph of monolayer $WS_2$ exfoliated in an organic solvent, and FIG. 7C is a TEM photograph of an aqueous solution of monolayer $WS_2$ functionalized with an amphiphilic block polymer compound through a phase transition method. From the two photographs, it was found that the surface of the exfoliated monolayer $WS_2$ was functionalized with an amphiphilic block polymer compound after the process of phase transition.

FIG. 8A to FIG. 8C show the optical properties (fluorescence, absorbance and Raman scattering properties) of monolayer TMDs functionalized with an amphiphilic block polymer compound by a phase transition method. FIG. 8A shows the fluorescence spectra of monolayer $WS_2$ exfoliated in an organic solvent and monolayer $WS_2$ functionalized with an amphiphilic block polymer compound in an aqueous solution through a phase transition method. From the spectra, it was found that the monolayer $WS_2$ obtained by a phase transition method maintained strong fluorescence properties. Also, from FIG. 8B, it was found that the monolayer $WS_2$ obtained by a phase transition method maintained the absorbance in the A-exciton region. Further, the Raman scattering analysis results showed that the Raman scattering signal of the monolayer $WS_2$ functionalized with an amphiphilic block polymer compound maintained the characteristic Raman scattering signal (FIG. 8C).

TEST EXAMPLE 4

Evaluation of Antioxidant Effects and the Stability of Antioxidant Effects

Figure 9A:
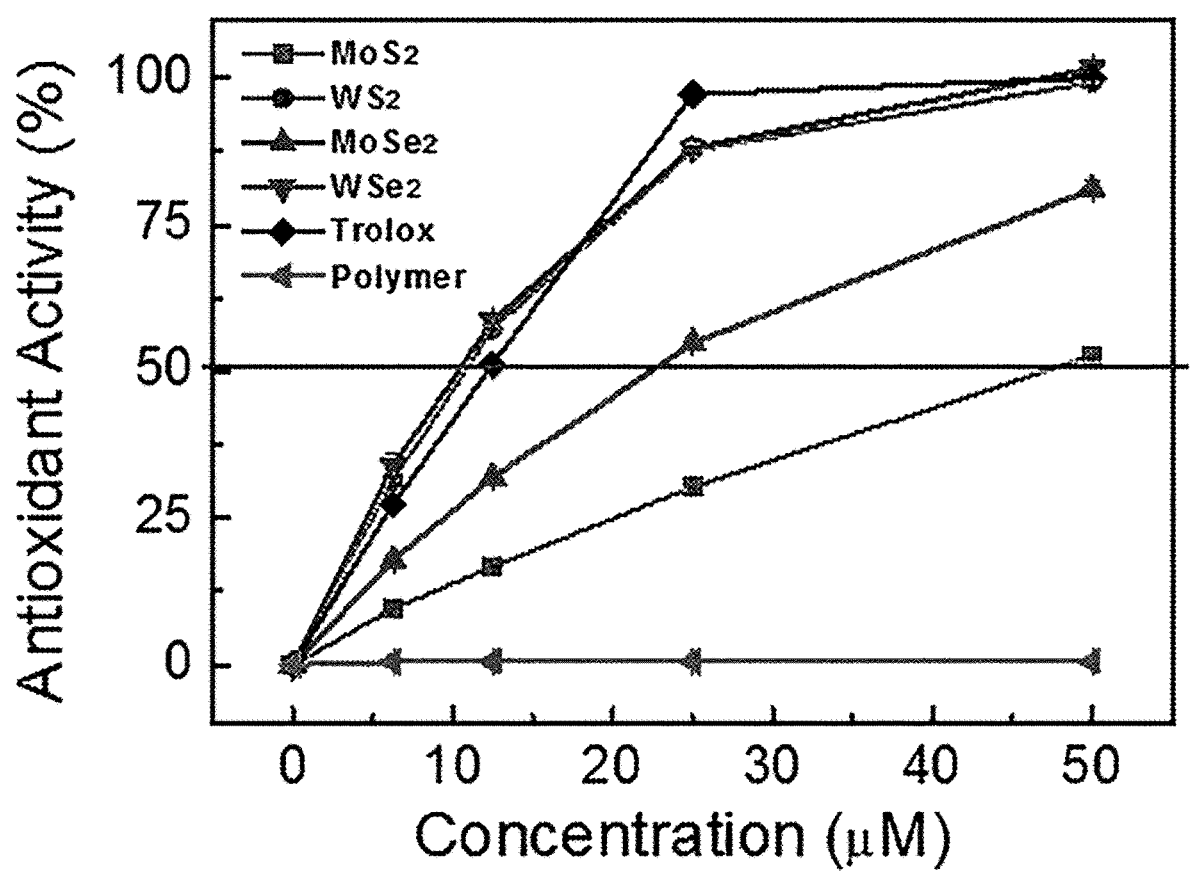
FIG. 9A and FIG. 9B show the evaluation results of the antioxidant effects and photostability of monolayer TMDs functionalized with an amphiphilic block polymer compound in an aqueous solution.
Figure 9B:
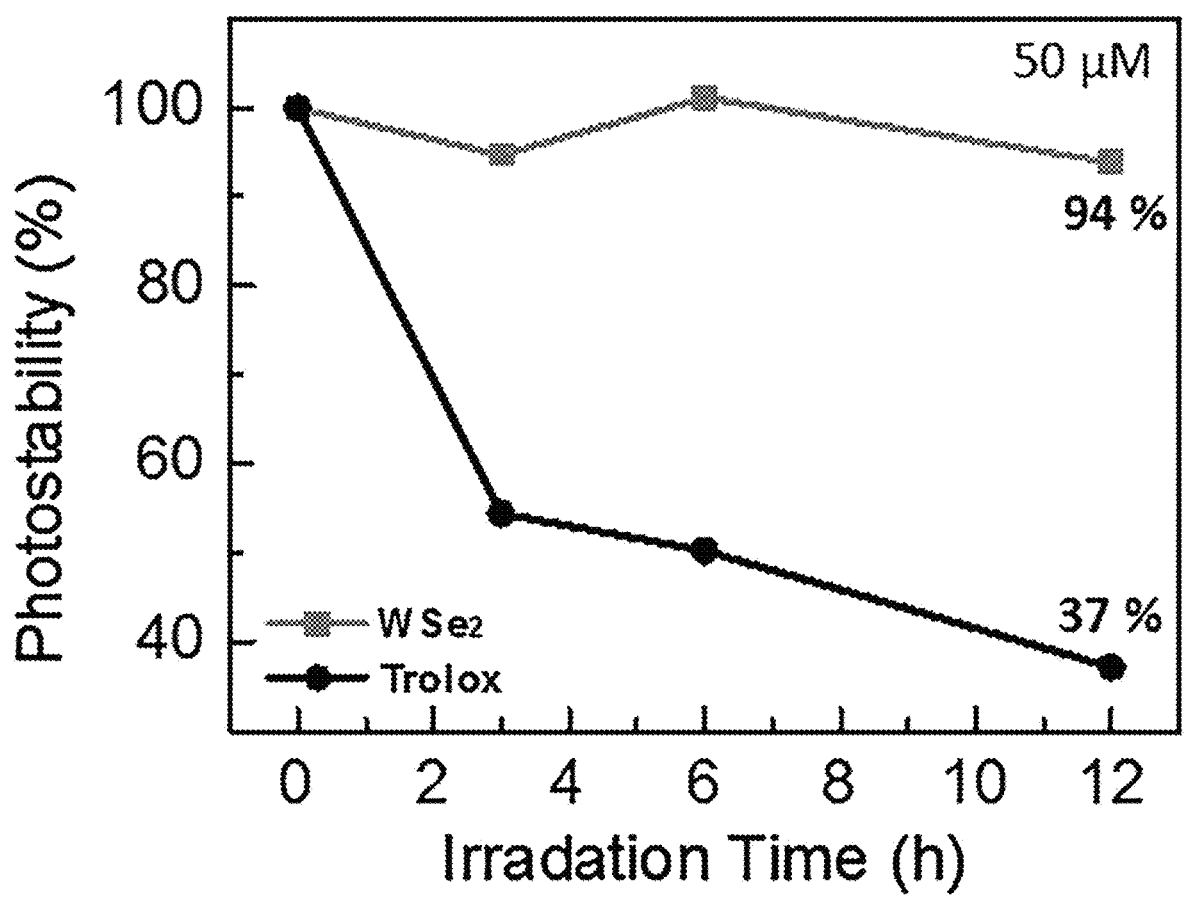

Monolayer TMDs (TMD antioxidants) functionalized with an amphiphilic block polymer compound in an aqueous solution was evaluated for antioxidant effects and photostability. The antioxidant effects and photostability of monolayer TMDs functionalized with an amphiphilic block polymer compound in an aqueous solution were compared with those of Trolox (vitamin E), and the results are shown in FIG. 9A and FIG. 9B.

Specifically, the antioxidant activity of four types of TMDs ($MoS_2$, $WS_2$, $MoSe_2$, and $WSe_2$) functionalized with an amphiphilic block polymer compound in an aqueous solution and Trolox (vitamin E) were measured by an ABTS (2,2'-azino-bis-(3-ethylbenzothiazoline-6-sulfonic acid)) assay.

Specifically, 7 mM 2,2'-azino-bis-(3-ethylbenzothiazoline-6-sulfonic acid) (ABTS) and 2.45 mM potassium persulfate were mixed to make the final concentration and left in a dark place at room temperature for 24 hours. Then, the mixture was diluted with distilled water so that the absorbance value at 734 nm was 73 (±0.1). 100 µl of the sample of each concentration was added to 100 µl of the diluted ABTS radical solution, followed by mixing. After 12 hours, the change of absorbance was measured. The same amount of Trolox as a standard material was added for measurement. $IC_{50}$ values were determined based on the results (FIG. 9A, Trolox: 11.7 µM, $MoS_2$: 36.3 µM, $WS_2$: 8.7 µM, $MoSe_2$: 16.2 µM, $WSe_2$: 9.2 µM).

From the fact that the amphiphilic polymer compound ("polymer" in FIG. 9A) used for exfoliation and dispersion has no antioxidant activity, it was found that the measured antioxidant properties were the inherent characteristic of TMDs. All the TMDs functionalized with an amphipathic polymer compound were found to exhibit antioxidant effects. In addition, the comparison results of $IC_{50}$ values showed that $WS_2$ and $WSe_2$ had better antioxidant activity than Trolox.

FIG. 9B shows the results of the evaluation of photostability (stability of the antioxidant activity as determined by ABTS assay) using the intensity (100 $mW/m^2$) of light actually received at the ground in a sunny weather by using a solar simulator. From the results, it was found that $WSe_2$ could maintain antioxidant activity for 12 hours or more, but that the antioxidant activity of Trolox decreased to 50% only after 3 hours. In other words, it was found that $WSe_2$ had a much better photostability than Trolox.

Figure 10A:
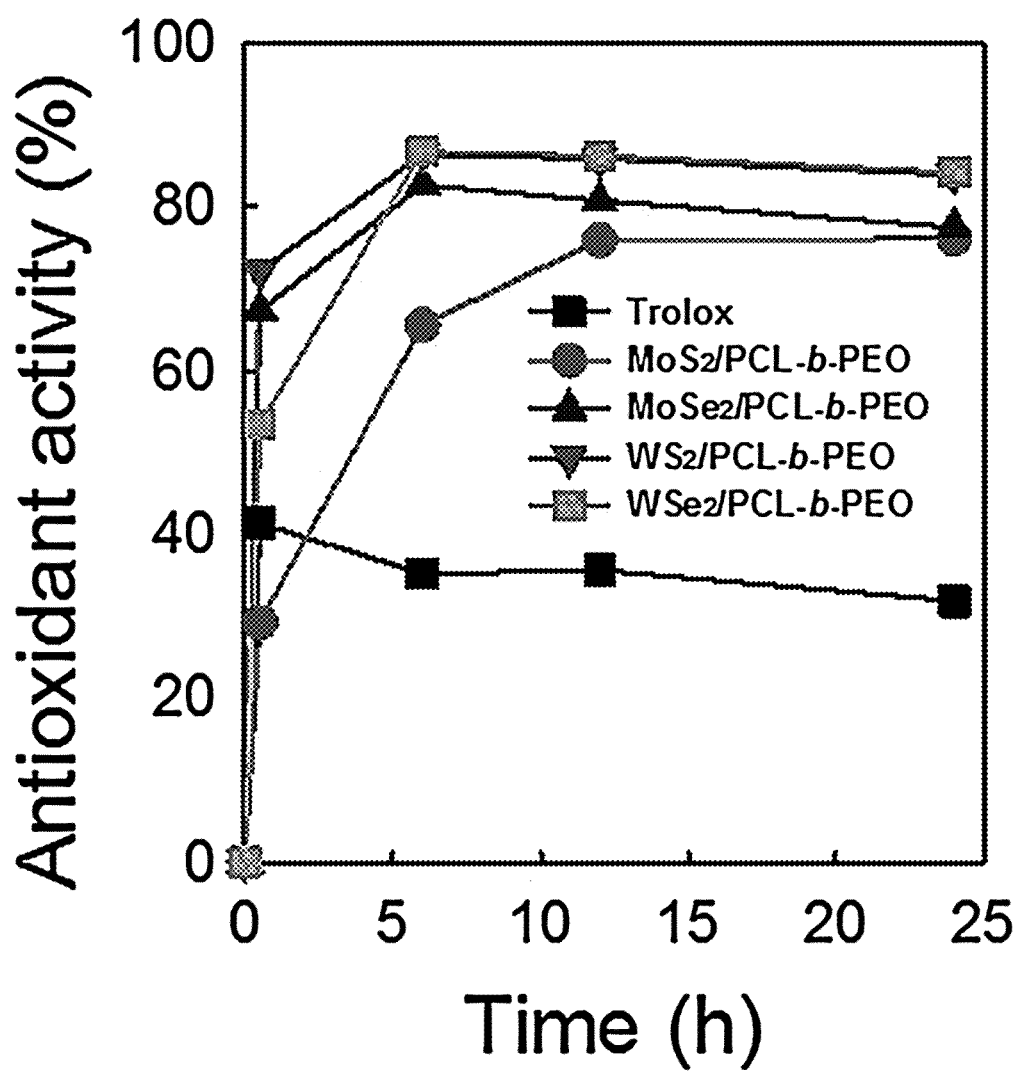
FIG. 10A and FIG. 10B show the evaluation results of the antioxidant effects, photostability and thermal stability of the monolayer TMDs functionalized with an amphiphilic block polymer compound according to Example 3.
Figure 10B:
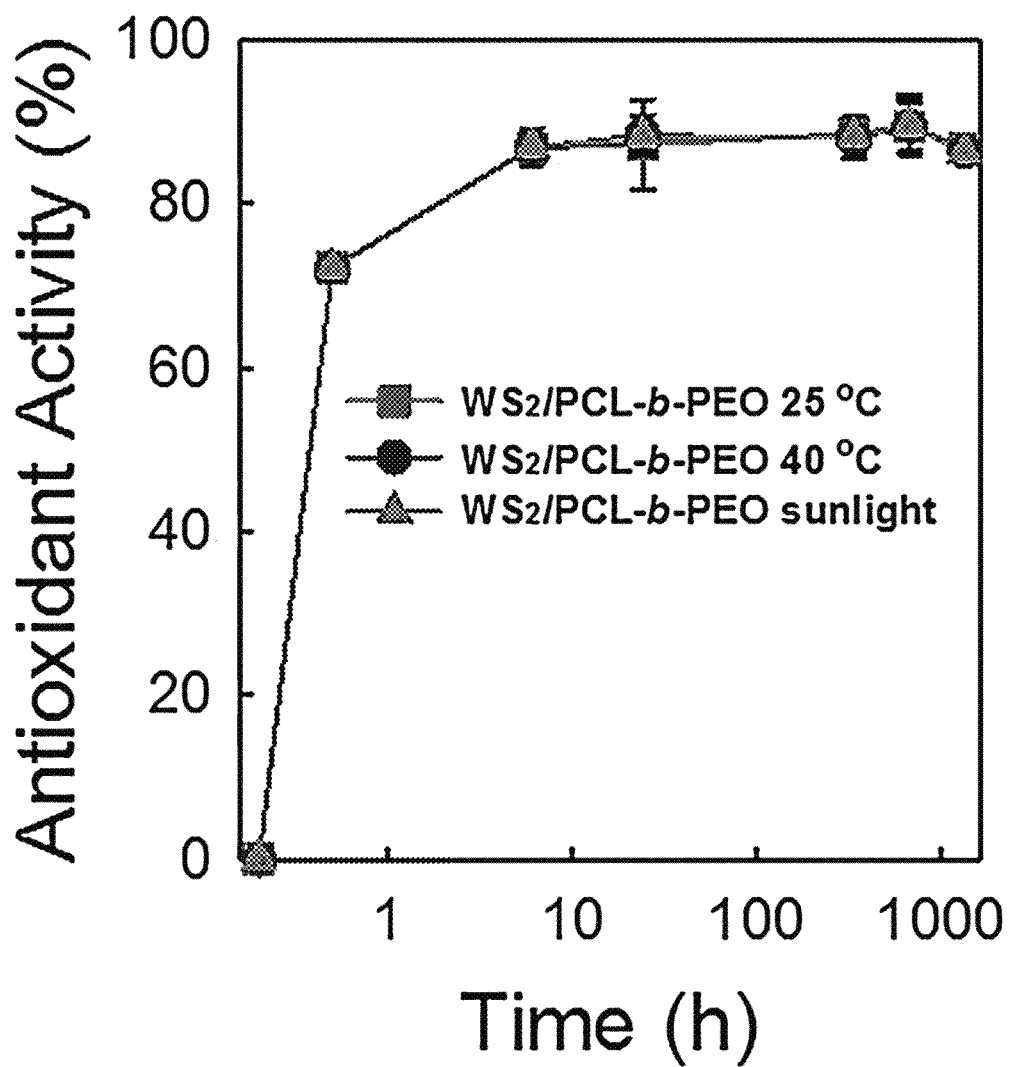

Meanwhile, monolayer TMDs (TMD antioxidants) functionalized with an amphiphilic block polymer compound, synthesized by a phase transition method, were also evaluated for antioxidant effects, photostability and thermal stability. Specifically, the antioxidant effects of four types of TMD antioxidants ($MoS_2$, $WS_2$, $MoSe_2$, and $WSe_2$) synthesized through a phase transition process and Trolox were measured by a method similar to the above. The results showed that all of the four antioxidants exhibited higher antioxidant activity than Trolox (FIG. 10A). In particular, $WS_2$ and $WSe_2$ showed excellent antioxidant activity. In order to evaluate the photostability, a $WS_2$ antioxidant was used as a representative example. A $WS_2$ antioxidant was placed by the window and exposed to sunlight. In order to evaluate the thermal stability, a $WS_2$ antioxidant was continuously exposed to heat at 40° C. The results showed that the $WS_2$ antioxidant maintained antioxidant activity without being influenced by external factors (FIG. 10B).

EXAMPLE 4

Preparation of Hydrogel for Antioxidation

In order to apply TMD antioxidants having excellent antioxidant activity to compositions for various purposes, a hydrogel carrying TMDs functionalized with an amphiphilic block polymer compound was prepared.

Specifically, the hydrogel raw material may be any raw material used in the art. However, in this Example, PEGDA (poly(ethylene glycol) diacrylate) was used. 1 g of PEGDA having a molecular weight of 700, 10 g of water, and 8.7 g of an aqueous solution containing 400 to 500 µM of TMDs functionalized with the amphiphilic block polymer compound as used herein were used to prepare a hydrogel carrying TMDs functionalized with an amphiphilic block polymer compound.

Figure 11A:
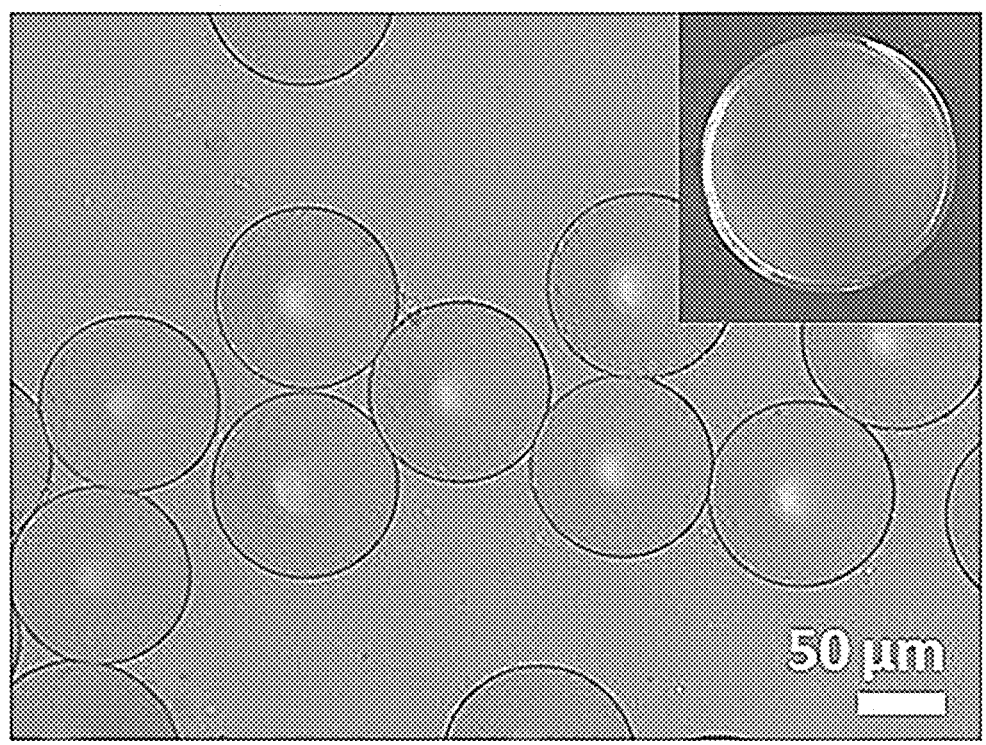
FIG. 11A and FIG. 11B show a hydrogel containing monolayer TMDs functionalized with an amphiphilic block polymer compound and its Raman scattering signals.

The shape of the hydrogel carrying $WS_2$ functionalized with an amphiphilic block polymer compound was observed from an optical microscope image (FIG. 11A). From the color change of the hydrogel, it was found that the $WS_2$ was carried in the hydrogel (inset).

Figure 11B:
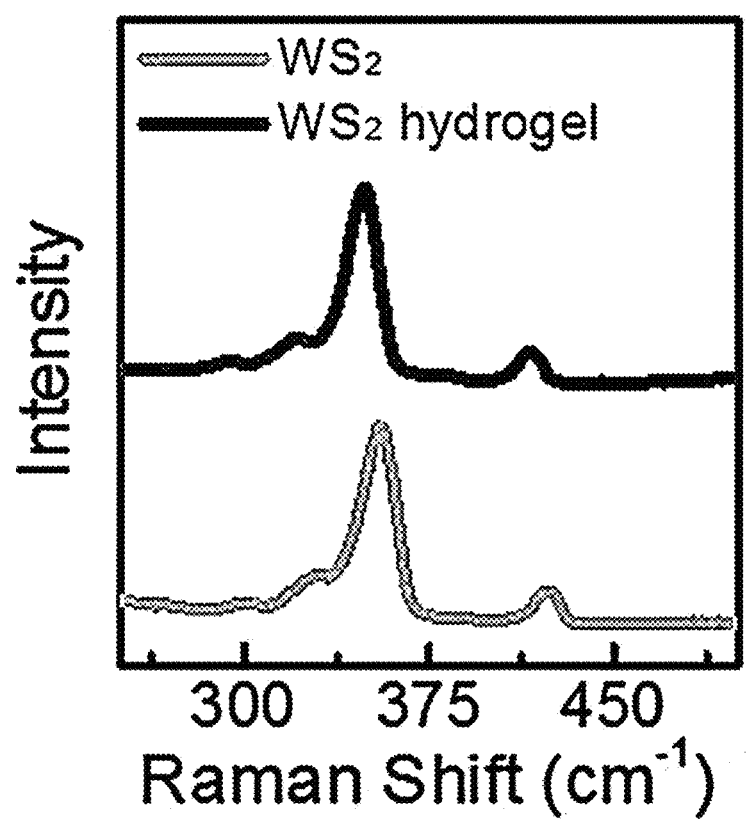

In addition, the hydrogel carrying monolayer $WS_2$ functionalized with a block polymer compound showed the characteristic Raman scattering signal of monolayer $WS_2$. Thus, it was understood that the hydrogel would retain the properties, antioxidant activity, stability, etc. of monolayer $WS_2$ (FIG. 11B). The hydrogels carrying TMDs other than $WS_2$ also showed similar results as in FIG. 11A and FIG. 11B.

Thus, it was found that it was possible to prepare a composition for antioxidation containing TMDs functionalized with an amphiphilic block polymer compound. In particular, it was found that the TMDs could be carried in a hydrogel, and thus could be applied to cosmetic compositions.

FORMULATION EXAMPLE 1

Cream Formulation 3.00% by weight of the dispersion according to Example 2 or Example 3, 2.00% by weight of polyethylene glycol monostearate, 5.00% by weight of self-emulsifying monostearate glycerin, 4.00% by weight of propylene glycol, 6.00% by weight of squalene, 6.00% by weight of tri-2-ethylhexane glyceryl, 1.00% by weight of sphingoglycolipid, 7.00% by weight of 1,3-butylene glycol, 5.00% by weight of beeswax, and a balance of purified water were used to prepare a cream formulation.

FORMULATION EXAMPLE 2

Pack 3.00% by weight of the dispersion according to Example 2 or Example 3, 13.00% by weight of polyvinyl alcohol, 1.00% by weight of L-ascorbic acid-2-phosphate magnesium salt, 1.00% by weight of lauroylhydroxyproline, 2.00% by weight of water-soluble collagen (1% aqueous solution), 3.00% by weight of 1,3-butylene glycol, 5.00% by weight of ethanol, and a balance of purified water to prepare a pack.

The transition metal dichalcogenides functionalized with an amphiphilic block polymer compound according to one aspect of the present invention can be stably dispersed in an aqueous solution. Also, the monolayer transition metal dichalcogenides exhibit excellent antioxidant effects and thus can be used as a new form of antioxidant material. Also, they are expected to be highly utilized in various fields including agents for external preparation to the skin, cosmetics, etc. which require the properties.

While the present invention has been described with respect to the specific embodiments, it will be apparent to those skilled in the art that various changes and modifications may be made without departing from the spirit and scope of the invention as defined in the following claims.

What is claimed is:

1. Monolayer transition metal dichalcogenides (TMDs) functionalized with an amphiphilic block polymer compound comprising a hydrophilic block and a hydrophobic block, wherein the amphiphilic block polymer compound contains polyethylene oxide (PEO) and poly(epsilon-caprolactone)(PCL), and the amphiphilic block polymer compound has the structure formula of following Formula 1:

[Formula 1]

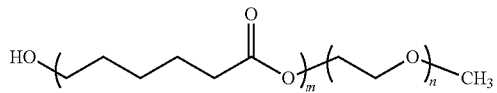

wherein m is an integer of 2 to 70 and n is an integer of 100 to 150, wherein the amphiphilic block polymer compound has a weight ratio of PCL:PEO of more than 1:1 and 1:20 or less.

2. The functionalized monolayer TMDs according to claim 1, wherein the amphiphilic block polymer compound has a weight average molecular weight of 3000 to 20,000.

3. The functionalized monolayer TMDs according to claim 1, wherein the TMDs are one or more selected from the group consisting of molybdenum disulfide ($MoS_2$), tungsten disulfide ($WS_2$), molybdenum diselenide ($MoSe_2$), and tungsten diselenide ($WSe_2$).

4. The functionalized monolayer TMDs according to claim 1, wherein the functionalized monolayer TMDs have a thickness of 1 to 10 nm.

5. The functionalized monolayer TMDs according to claim 1, wherein the functionalized monolayer TMDs are dispersed in a medium.

6. The functionalized monolayer TMDs according to claim 5, wherein the medium is an aqueous solution or an oil-in-water (O/W) emulsion.

7. A method for antioxidation, which comprises administering an effective amount of the functionalized monolayer TMDs according to claim 1 in a form of a composition to a subject in need thereof.

8. The method for antioxidation according to claim 7, wherein the composition is a cosmetic composition.

9. A method for preparing the functionalized monolayer TMDs according to claim 1, comprising the processes of:
mixing an amphiphilic block polymer compound and TMD with water; and
exfoliating the TMDs during or after the mixing process.

10. The preparation method according to claim 9, wherein the exfoliation is performed ultrasonically.

11. A method for preparing the functionalized monolayer TMDs according to claim 1, comprising the processes of:
dispersing TMDs in an organic solvent;
dispersing an amphiphilic block polymer compound in an organic solvent separate from the organic solvent; and
mixing the solution in which the TMDs are dispersed and the solution in which the amphiphilic block polymer compound is dispersed and then mixing water therewith.

12. The preparation method according to claim 11, wherein the process of mixing water causes a phase transition.

13. The preparation method according to claim 11, wherein the organic solvent for dispersing the TMDs or the organic solvent for dispersing the amphiphilic block polymer compound is one or more selected from the group consisting of an aprotic solvent, a C1 to C5 alcohol, a C1 to C5 ketone, and mixtures thereof.

14. The preparation method according to claim 11, further comprising the process of removing the organic solvent for dispersing the TMDs and the organic solvent for dispersing the amphiphilic block polymer compound after the process of mixing water.

* * * * *